(12) United States Patent
Denny et al.

(10) Patent No.: US 7,276,537 B2
(45) Date of Patent: *Oct. 2, 2007

(54) FORMULATIONS OF ANTHRAQUINONE DERIVATIVES

(75) Inventors: William Alexander Denny, Auckland (NZ); Laurence Hylton Patterson, Leicester (GB); Gavin William Halbert, Glasgow (GB); Steven John Ford, Glasgow (GB)

(73) Assignee: BTG International Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/433,545

(22) Filed: May 15, 2006

(65) Prior Publication Data

US 2006/0205820 A1    Sep. 14, 2006

Related U.S. Application Data

(63) Continuation of application No. 10/507,483, filed as application No. PCT/GB03/01110 on Mar. 17, 2003, now Pat. No. 7,074,835.

(30) Foreign Application Priority Data

Mar. 15, 2002 (GB) .................................. 0206255.2

(51) Int. Cl.
| | |
|---|---|
| C07C 291/04 | (2006.01) |
| A61K 47/02 | (2006.01) |
| A61K 47/12 | (2006.01) |
| A61P 35/00 | (2006.01) |

(52) U.S. Cl. ................ 514/644; 552/246; 552/247
(58) Field of Classification Search ............... 552/246, 552/247; 514/644
See application file for complete search history.

(56) References Cited

U.S. PATENT DOCUMENTS

| 5,132,327 | A  | 7/1992  | Patterson ............ 514/644 |
| 6,320,063 | B1 | 11/2001 | Denny et al. ........ 552/247 |

FOREIGN PATENT DOCUMENTS

| GB | 2237283 A | 5/1991 |
| WO | WO91/05824 | 5/1991 |
| WO | WO 00/05194 | 2/2000 |
| WO | WO 2005/025537 | 3/2005 |

OTHER PUBLICATIONS

Patterson, et al; *British Journal of Cancer*; 82(12), 1984-1990, 2000.
Patterson, et al; *British Journal of Cancer*; 83(12), 1589-1593, 2000.
Loadman, P.M., et al; "A Preclinical Pharmacokinetic Study of the Bioreductive Drug AQ4N"; *Drug Metabolism and Disposition*; vol. 29, No. 4 Part 1; pp. 422-426; (See pg. 423, col. 1, lines 13-16; Table 1) XP002306883 (2001).
Loadman, P.M., et al; "Separation methods for anthraquinone related anti-cancer drugs"; *Journal of Chromatography B: Biomedical Sciences & Applications*, Elsevier Science Publ, NL; vol. 764, No. 1-2, pp. 193-206 (whole document) XP004322153 (2001).
Lee, Ho H. et al.; "A Large-scale Synthesis of the Bioreductive Drug 1,4-Bis{'2-(dimethylamino)ethyl!amino}-5,8-dihydroxyanthracene-9,10-dione bis-N-oxide"; *Journal of the Chemical Society*, Perkin Transactions 1, 1999; pp. 2755-2758; XP002244552; Chemical Society, Letchworth., GB ISSN: 0300-922X.

*Primary Examiner*—Fiona T Powers
(74) *Attorney, Agent, or Firm*—Nixon & Vanderhye

(57) ABSTRACT

A compound of formula (I): in which A is a C alkylene group with a chain length between NH and N(O)R'R" of at least 2 carbon atoms and R' and R" are each separately selected from $C_{1-4}$ alkyl groups and $C_{2-4}$ hydroxyalkyl and $C_{2-4}$ dihydroxyalkyl groups, or R' and R" together are a $C_{2-6}$ alkylene group, is formulated so that upon dissolution in aqueous solution the pH of the solution is in the range of 5 to 9. The compound may be in the form of salt with a physiologically acceptable acid having a $pK_a$ in the range of −3.0 (minus 3.0) to 9.0

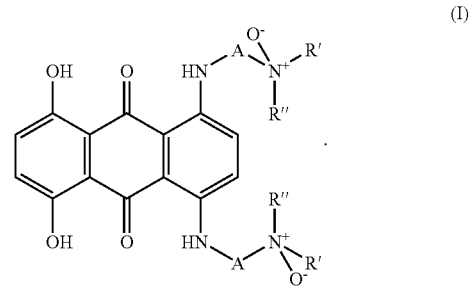

(I)

14 Claims, 4 Drawing Sheets

AQ4N → AQ4N salt ] 2 x Acid

Malonic acid

Maleic acid

L-(+)-Tartaric acid

Dichloroacetic acid

Pimelic acid

Benzenesulfonic acid

Acetic acid

DL-Lactic acid

Citric acid

FORMULATIONS OF ANTHRAQUINONE DERIVATIVES

This application is a continuation of application Ser. No. 10/507,483, filed Sep. 27, 2004, now U.S. Pat. No. 7,074,835, which is a 371 of PCT/GB03/01110, filed Mar. 17, 2003, the entire content of which is hereby incorporated by reference in this application.

The invention relates to novel formulations of anthraquinone derivatives such as AQ4N, a bis-bioreductive agent with value in the treatment of cancer. It includes novel salt forms of the anthraquinone derivatives.

WO-A-91/05824 (National Research Development Corporation) discloses a compound of formula:

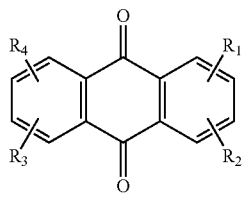

in which $R_1$, $R_2$, $R_3$ and $R_4$ are each separately selected from hydrogen, X, NH-A-NHR and NH-A-N(O)R'R" wherein X is hydroxy, halogeno, amino, $C_{1-4}$ alkoxy or $C_{2-8}$ alkanoyloxy, A is a C alkylene group with a chain length between NH and NHR or N(O)R'R" of at least 2 carbon atoms and R, R' and R" are each separately selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, the compound optionally being in the form of a physiologically acceptable salt.

A preferred compound within this general formula is the N-oxide AQ4N, which would normally be synthesised by oxidation of AQ4:

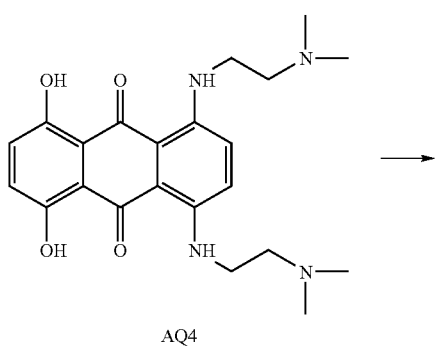

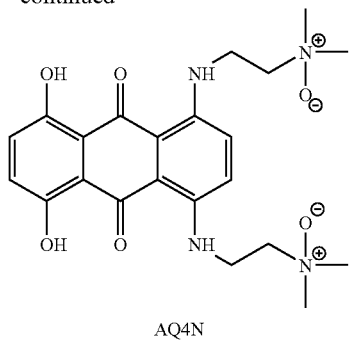

AQ4N is in fact a prodrug and the reverse reaction occurs in vivo, reductive metabolism in hypoxic cancer cells giving the active agent, AQ4, in its protonated form. The prodrug is relatively non-toxic when compared with the active agent, AQ4, making it particularly attractive for administration as a pharmaceutical. However, it does not readily give a crystalline form, and it is therefore desirable to prepare and formulate it for administration in the form of a salt.

AQ4N has up to now been reported in the form of a dihydrochloride salt AQ4N.2HCl. See for example *J. Chem. Soc., Perkin Trans. I*, 1999, 2755-2758 (Lee et al.) and WO-A-00/05194 (BTG International Limited). However, investigations of AQ4N.2HCl raw material have demonstrated significant quantities of an impurity 1-amino-4-{[2-(dimethylamino)ethyl]amino}-5,8-dihydroxyanthraquinone, denoted AQMN, which has been characterised by LCMS:

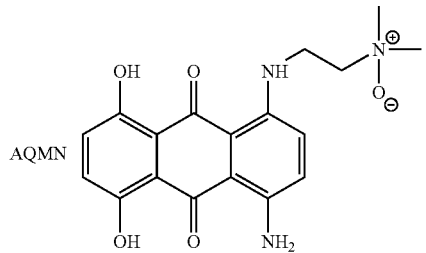

This impurity can be formed by degradation of AQ4N, and more significantly shows an undesirable level of cytotoxicity, generally being higher than that of AQ4N itself. This level of cytotoxicity is to be avoided in a compound which is intended to be administered in the form of a relatively non-toxic prodrug.

Although the AQMN degradation is the predominant pathway, a further degradation product of AQ4N under acidic and neutral aqueous solution conditions is the mono-N-oxide, AQ4M:

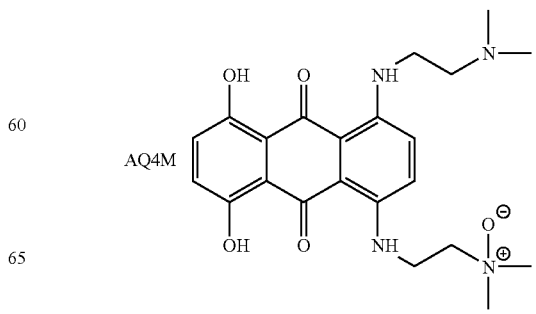

We have determined that the dihydrochloride salt AQ4N in aqueous solution typically gives a pH of around 2 to 3. For example, a 1.4 millimolar solution has a pH of 2.4. We have now found that the above problem with impurity formation may be reduced or avoided by preparing, formulating and administering the compound so that upon dissolution in solution, the pH of the solution is in the range of 5 to 9.

Thus according to the present invention there is provided a compound of formula (I):

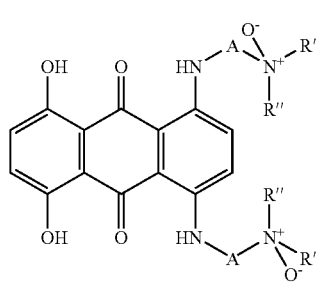

(I)

in which A is a C alkylene group with a chain length between NH and N(O)R'R" of at least 2 carbon atoms and R' and R" are each separately selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-4}$ alkylene group which with the nitrogen atom to which R' and R" are attached forms a heterocyclic group having 3 to 7 atoms in the ring, characterised in that the compound is formulated so that upon dissolution in aqueous solution the pH of the solution is in the range of 5 to 9.

Preferably the compound is formulated so that upon dissolution in aqueous solution the pH of the solution is in the range of 6 to 8.

Preferably the compound is formulated so that upon dissolution in aqueous solution at a concentration of between 0.1 and 100 mg/ml the pH of the solution is in the specified range.

The compounds (I) may be used in the form of a physiologically acceptable salt which will be an acid addition salt with an organic or inorganic acid. Preferably the physiologically acceptable acid has a $pK_a$ in the range of −3.0 (minus 3.0) to 9.0, and more preferably in the range of 2.0 to 9.0. More preferably the physiologically acceptable acid has a $pK_a$ in the range of 2.0 to 6.0.

Preferably the physiologically acceptable acid is selected from the group consisting of tartaric acid, malonic acid, dichloroacetic acid, citric acid, maleic acid, benzenesulfonic acid, pimelic acid and acetic acid.

More preferably the physiologically acceptable acid has a $pK_a$ in the range of 3.0 to 6.0. The physiologically acceptable acid may especially be an organic acid, particularly an organic mono-, di- or tri-acid, and especially one selected from the group consisting of tartaric acid, citric acid, pimelic acid and acetic acid.

A in formula (I) may be branched but is conveniently a straight chain alkylene group, i.e. tetramethylene, especially trimethylene, or particularly ethylene.

R' and R" may also have a branched carbon chain but are conveniently straight chain whether they are alkyl groups or hydroxy-substituted alkyl groups. When R' or R" is a mono-hydroxyalkyl group this is conveniently substituted terminally and when R' or R" is a dihydroxyalkyl group this is conveniently substituted terminally by one of the hydroxy groups. When R' and R" are alkyl the preference is for a group of three or especially two or one carbon atoms and when R' and R" are hydroxy-substituted alkyl the preference is for the alkyl group to be of three carbon atoms or, in the case of a monohydroxyalkyl group, alternatively of two carbon atoms. Examples of preferred individual groups R' and R" are $CH_3$, $CH_2CH_3$, $CH_2CH_2CH_3$, $CH_2CH_2OH$, $CH_2CH_2CH_2OH$, $CH(CH_3)CH_2OH$ and $CH_2CHOHCH_2OH$.

R' and R" will more usually be identical.

Alternatively, as indicated, R' and R" together with the nitrogen atom to which they are attached may represent a heterocyclic group —$N(CH_2)_n$ where n is 2 to 6, i.e. aziridin-1-yl, azetidin-1-yl, pyrrolidin-1-yl, piperidin-1-yl and perhydroazepin-1-yl, the smaller groups such as azetidin-1-yl and especially aziridin-1-yl being of most interest.

Specific groups NH-A-N(O)R'R" of particular interest are NH—$(CH_2)_2$—N(O)$(CH_3)C_2H_5$, NH—$(CH_2)_2$—N(O)$(C_2H_5)_2$, NH—$(CH_2)_2$—N(O)$(CH_2CH_2OH)_2$, NH—$(CH_2)_2$—N(O)$(CH_2CH_2CH_2OH)_2$, NH—$(CH_2)_2$—N(O)$(CH(CH_3)CH_2OH)_2$, NH—$(CH_2)_2$—N(O)$(CH_2CHOHCH_2OH)_2$ especially NH—$(CH_2)_2$—N(O)$(CH_3)_2$.

The physiologically acceptable salt when simply dissolved in aqueous solution will normally give a solution having a pH lower than the desired range. For example, the acetate salt of AQ4N in a 1.4 millimolar solution aqueous solution has a pH of 3.8. Thus preferably the compound is formulated in a mixture containing additional components so that upon dissolution in aqueous solution the pH of the solution is buffered to be in the range of 5 to 9.

A buffer is a solvated mixture of salt and acid, which oppose changes in pH when small amounts of acid and bases are added to the solution. Suitable buffers include sodium acetate buffer and sodium orthophosphate buffer.

According to a further aspect of the present invention there is provided an aqueous solution of a compound of formula (I), characterised in that the pH of the solution is in the range of 5 to 9.

Certain new salt forms may be used in the present invention. If they are salts of an acid having a $pK_a$ higher than that of hydrochloric acid (approximately −6, i.e. minus 6), then they will be easier to formulate as a solid mixture containing additional components which buffer the pH when in aqueous solution, as compared to the dihydrochloride salt, since they are less acidic.

Thus according to a further aspect of the present invention there is provided a compound of formula (I):

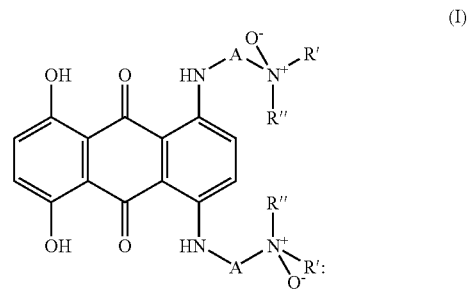

(I)

in which A is a C alkylene group with a chain length between NH and N(O)R'R" of at least 2 carbon atoms and R' and R"

are each separately selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, characterised in that the compound is in the form of a salt with a physiologically acceptable acid having a $pK_a$ in the range of −73.0 (minus 3.0) to 9.0.

Preferably the physiologically acceptable acid has a $pK_a$ in the range of 2.0 to 9.0. More preferably the physiologically acceptable acid has a $pK_a$ in the range of 2.0 to 6.0.

The salts would generally be capably of being formed as anhydrous salts, and may be more stable as crystalline solids than to the dihydrochloride salt which would have water of crystallisation present. The salts would be easy to obtain in pure form.

The compounds (I) will be used in the form of a physiologically acceptable salt which will be an acid addition salt with an organic or inorganic acid. Physiologically acceptable acids having a $pK_a$ in the range of −3.0 to 9.0 may be drawn from the following Table 1:

TABLE 1

$pK_a$ values of some common acids

| Free Acid or Base | $pK_a$ at 25° C. |
|---|---|
| Benzenesulfonic | −2.50 |
| p-Toluenesulfonic | −1.34 |
| Methanesulfonic | −1.2 |
| Dichloroacetic | 1.25 |
| Maleic | 2.00 ($pK_{a1}$) |
| Benzenehexacarboxylic (mellitic) | 2.08 ($pK_{a1}$) |
| Phosphoric | 2.12 ($pK_{a1}$) |
| Brucine tetrahydrate | 2.30 ($pK_{a1}$) |
| Benzenepentacarboxylic | 2.34 ($pK_{a1}$) |
| Glycine | 2.34 ($pK_{a1}$) |
| Benzene-1,2,4,5-tetracarboxylic (pyromellitic) | 2.43 ($pK_{a1}$) |
| Malonic | 2.85 ($pK_{a1}$) |
| Phthalic | 2.90 |
| Salicylic | 2.98 |
| Benzene-1,2,3-tricarboxylic (hemimellitic) | 2.98 ($pK_{a1}$) |
| Tartaric | 3.02 ($pK_{a1}$) |
| Fumaric | 3.03 ($pK_{a1}$) |
| Glycylglycine | 3.06 |
| Cyclopentanetetra-1,2,3,4-carboxylic | 3.07 ($pK_{a1}$) |
| o-Phthalic | 3.10 ($pK_{a1}$) |
| Citric | 3.13 ($pK_{a1}$) |
| Benzene-1,2,4,5-tetracarboxylic (pyromellitic) | 3.13 ($pK_{a1}$) |
| Benzene-1,3,5-tricarboxylic (trimesic) | 3.16 ($pK_{a1}$) |
| Glucuronic | 3.18 |
| Dimethylmalonic | 3.29 ($pK_{a1}$) |
| Mandelic | 3.36 |
| Butane-1,2,3,4-tetracarboxylic | 3.36 ($pK_{a1}$) |
| Malic | 3.40 ($pK_{a1}$) |
| 1,1-Cyclohexanediacetic | 3.52 ($pK_{a1}$) |
| 2-Methylpropane-1,2,3-triscarboxylic | 3.53 ($pK_{a1}$) |
| Hippuric | 3.64 |
| Propane-1,2,3-tricarboxylic (tricarballylic) | 3.67 ($pK_{a1}$) |
| Formic | 3.75 |
| Gluconic | 3.76 |
| 3,3-Dimethylglutaric | 3.79 ($pK_{a1}$) |
| 1,1-Cyclopentanediacetic | 3.82 ($pK_{a1}$) |
| Itaconic | 3.84 ($pK_{a1}$) |
| Lactic | 3.86 |
| Barbituric | 3.98 |
| Ascorbic | 4.10 ($pK_{a1}$) |
| 2,2-Dimethylsuccinic | 4.11 ($pK_{a1}$) |
| Succinic | 4.19 ($pK_{a1}$) |
| Benzoic | 4.20 |
| 3,6-Endomethylene-1,2,3,6-tetrahydrophthalic "EMTA" | 4.30 ($pK_{a1}$) |
| 2,2-Dimethylglutaric | 4.31 ($pK_{a1}$) |

TABLE 1-continued $pK_a$ values of some common acids

| Free Acid or Base | $pK_a$ at 25° C. |
|---|---|
| Pimelic | 4.48 |
| Acetic | 4.75 |
| Sorbic | 4.76 |
| n-Butyric | 4.82 |
| Propionic | 4.87 |
| Malic | 5.05 ($pK_{a2}$) |
| Pyridine | 5.23 |
| Hydroxylamine | 6.03 |
| Edetic | 6.16 ($pK_{a3}$) |
| Carbonic | 6.35 ($pK_{a1}$) |
| Citric | 6.40 ($pK_{a3}$) |
| Bis(2-hydroxyethyl)iminotris(hydroxymethyl)methane "BIS-TRIS" | 6.46 |
| Imidazole | 7.00 |
| 2-(Aminoethyl)trimethylammonium chloride "CHOLAMINE" | 7.10 |
| Phosphoric | 7.21 ($pK_{a2}$) |
| 2-Hydroxyethyliminotris(hydroxymethyl)methane "MONO-TRIS" | 7.83 |
| 4-(2-Hydroxyethyl)-1-piperazinepropane sulfonic "EPPS" | 8.00 |

Preferably the physiologically acceptable acid is selected from the group consisting of tartaric acid, malonic acid, dichloroacetic acid, citric acid, maleic acid, benzenesulfonic acid, pimelic acid and acetic acid.

More preferably the physiologically acceptable acid has a $pK_a$ in the range of 3.0 to 6.0. The physiologically acceptable acid may especially be an organic acid, particularly an organic mono-, di- or tri-acid, and especially one selected from the group consisting of tartaric acid, citric acid, pimelic acid and acetic acid.

A in formula (I) may be branched but is conveniently a straight chain alkylene group, i.e. tetramethylene, especially trimethylene, or particularly ethylene.

R' and R" may also have a branched carbon chain but are conveniently straight chain whether they are alkyl groups or hydroxy-substituted alkyl groups. When R' or R" is a monohydroxyalkyl group this is conveniently substituted terminally and when R' or R" is a dihydroxyalkyl group this is conveniently substituted terminally by one of the hydroxy groups. When R' and R" are alkyl the preference is for a group of three or especially two or one carbon atoms and when R' and R" are hydroxy-substituted alkyl the preference is for the alkyl group to be of three carbon atoms or, in the case of a monohydroxy alkyl group, alternatively of two carbon atoms. Examples of preferred individual groups R' and R" are $CH_3$, $CH_2CH_3$, $CH_2CH_2CH_3$, $CH_2CH_2OH$, $CH_2CH_2CH_2OH$, $CH(CH_3)CH_2OH$ and $CH_2CHOHCH_2OH$.

R' and R" will more usually be identical.

Alternatively, as indicated, R' and R" together with the nitrogen atom to which they are attached may represent a heterocyclic group—$N(CH_2)_n$ where n is 2 to 6, i.e. aziridin-1-yl, azetidin-1-yl, pyrrolidin-1-yl, piperidin-1-yl and perhydroazepin-1-yl, the smaller groups such as azetidin-1-yl and especially aziridin-1-yl being of most interest.

Specific groups NH-A-N(O)R'R" of particular interest are NH—$(CH_2)_2$—N(O)($CH_3$)$C_2H_5$, NH—$(CH_2)_2$—N(O)($C_2H_5$)$_2$, NH—$(CH_2)_2$—N(O)($CH_2CH_2OH$)$_2$, NH—$(CH_2)_2$—N(O)($CH_2CH_2CH_2SH$)$_2$, NH—$(CH_2)_2$—N(O)(CH($CH_3$)$CH_2OH$)$_2$, NH—$(CH_2)_2$—N(O)($CH_2CHOHCH_2OH$)$_2$ especially NH—$(CH_2)_2$—N(O)($CH_3$)$_2$.

The salt with a physiologically acceptable acid may be prepared by any conventional means, for example by reaction of the organic base (I) with the appropriate inorganic or organic acid, usually by simple admixture in solution. The acid addition salts are generally crystalline solids which are relatively soluble in water methanol, ethanol and similar solvents. One salt form may also be converted into another by chromatography using a column which has been pre-treated with the desired physiologically acceptable acid.

The compounds (I) may be formulated with a physiologically acceptable diluent or carrier for use as pharmaceuticals for both veterinary and particularly human use by a variety of methods. For instance, they may be applied as a composition incorporating a liquid diluent or carrier, for example an aqueous solution, suspension or emulsion, which may often be employed in injectable form for parenteral administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules. Alternative, more specialized types of formulation include liposomes and nanoparticles.

Other types of administration than by injection or through the oral route which are of use in both human and veterinary contexts include the use of suppositories or pessaries. Another form of pharmaceutical composition is one for buccal or nasal administration or alternatively drops for administration into the eye which may conveniently contain a sterile liquid diluent or carrier. Other formulations for topical administration include lotions, ointments, creams, gels and sprays.

Compositions may be formulated in unit dosage form, i.e. in the form of discrete portions containing a unit dose, or a multiple or sub-unit of a unit dose.

Whilst the dosage of the compound used will vary according to the activity of (the particular compound and the condition being treated, it may be stated by way of guidance that a dosage selected in the range from 25-500 mg/m$^2$ per day, particularly in the range from 50-300 mg/m$^2$ per day, will often be suitable although higher doses than this, for example in the range from 25-750 mg/m$^2$ per day, or even doses up to 1200 mg/m$^2$, may be considered in view of the lower level of toxic side effects obtained with the compounds (I). This dosage regime may be continued for however many days is appropriate to the patient in question, the daily dosages being divided into several separate administrations if desired. Thus, for example, in the case of conditions such as advanced breast cancer, non-Hodgkin's lymphoma and hepatoma, treatment for one day followed by a repeated dose after an interval, such as 21 days, may be appropriate whilst for the treatment of acute non-lymnphocytic leukaemia, treatment over 5 consecutive days may be more suitable. Alternatively, single administrations spaced by several days, for example one dose every two or three weeks, may be used.

The compounds (I) are of particular value for the treatment of cancer in warm blooded animals including humans. The compounds are of interest in relation to the treatment of solid tumours, such as various forms of sarcoma and carcinoma, and also for disseminated tumours such as leukaemias. Areas of particular interest are the treatment of breast cancer, lung cancer, prostate cancer, pancreatic cancer, and oesophageal cancer, and the treatment of non-Hodgkin's lymphoma and acute non-lymphocytic leukaemia. In the treatment of cancer, parenteral and sometimes topical administration is often of particular interest. Moreover, it may be advantageous to use the compounds (I) in a combined treatment, given separately or together in the same composition, with other anti-cancer agents, such as mitotic inhibitors, for example vinblastine; alkylating agents, for example cisplatin, carboplatin and cyclo-phosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon. The compounds (I) may also be used in combined treatment with radiation therapy of the tumour.

The present invention thus includes a method for aiding regression and palliation of cancer which comprises administering to a patient a therapeutically effective amount of a compound (I) as defined hereinbefore.

In addition to their anti-cancer use the compounds (I) are of interest for various other pharmaceutical applications in view of their activity as chelating agents.

The invention is illustrated by the following Examples in which—

Figure 6:
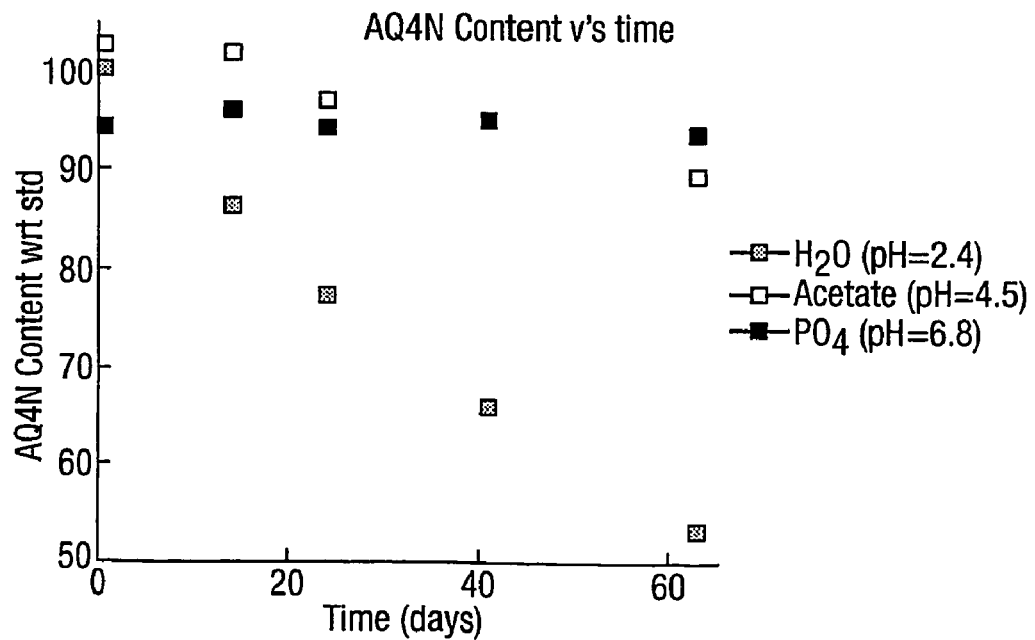
Figure 7:
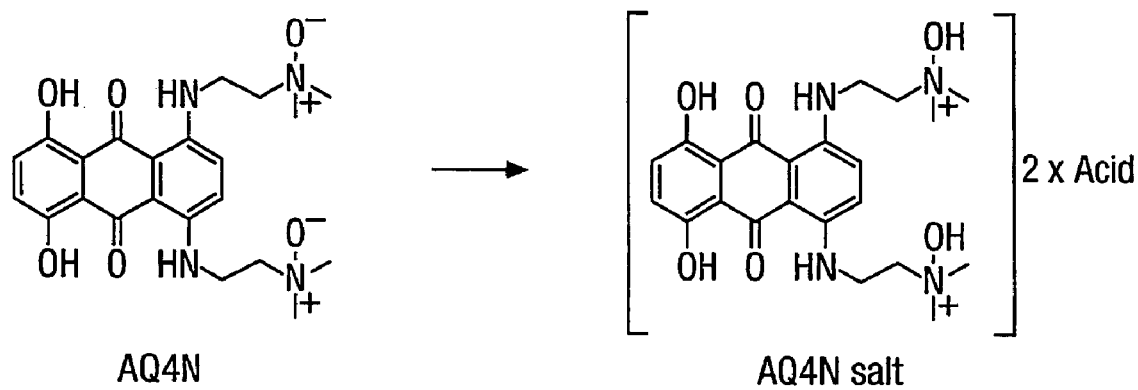

FIG. 6. shows the decrease in AQ4N over incubation time in 5 mg/ml solutions incubated at 40° C. for 63 days;

FIG. 7 shows the formal method used to prepare salts of AQ4N; and

Figure 8:
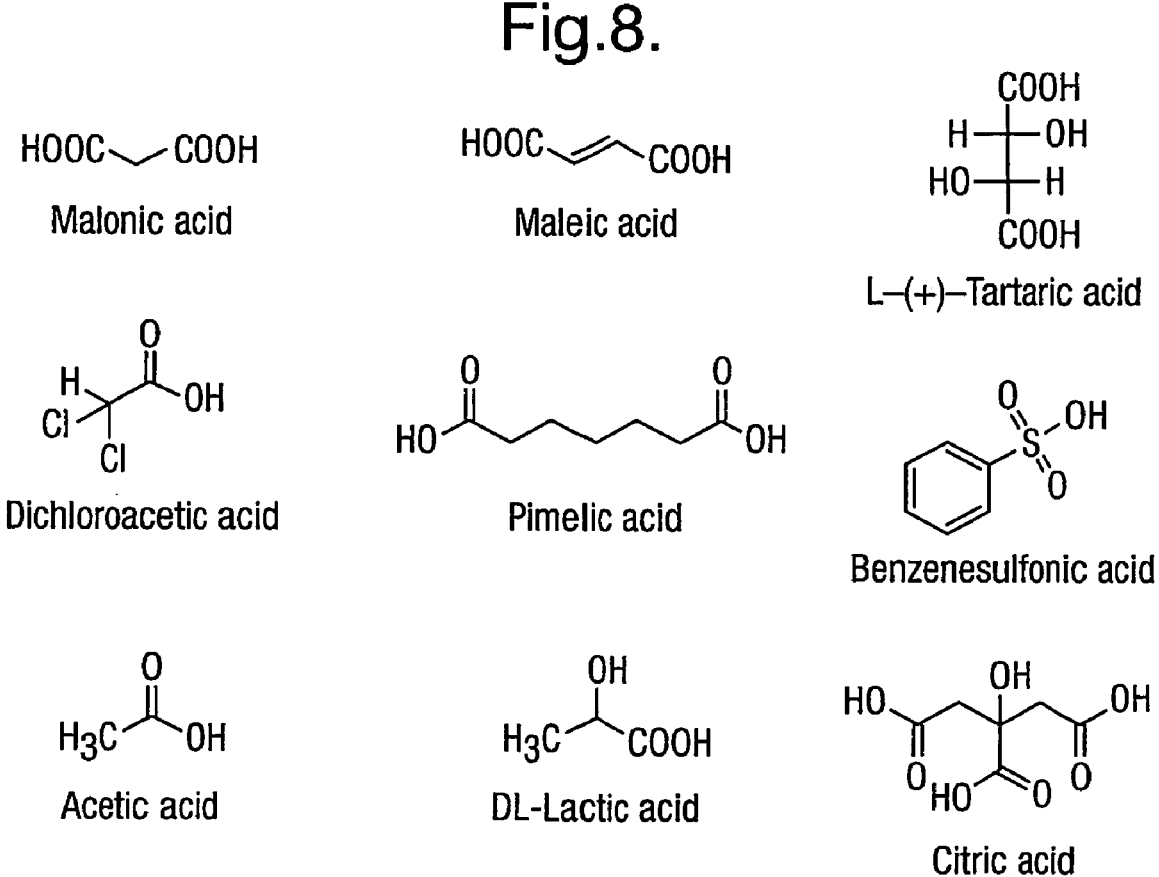

FIG. 8 shows the organic acids used to prepare salts of AQ4N.

EXAMPLES

Example 1

Figure 1:
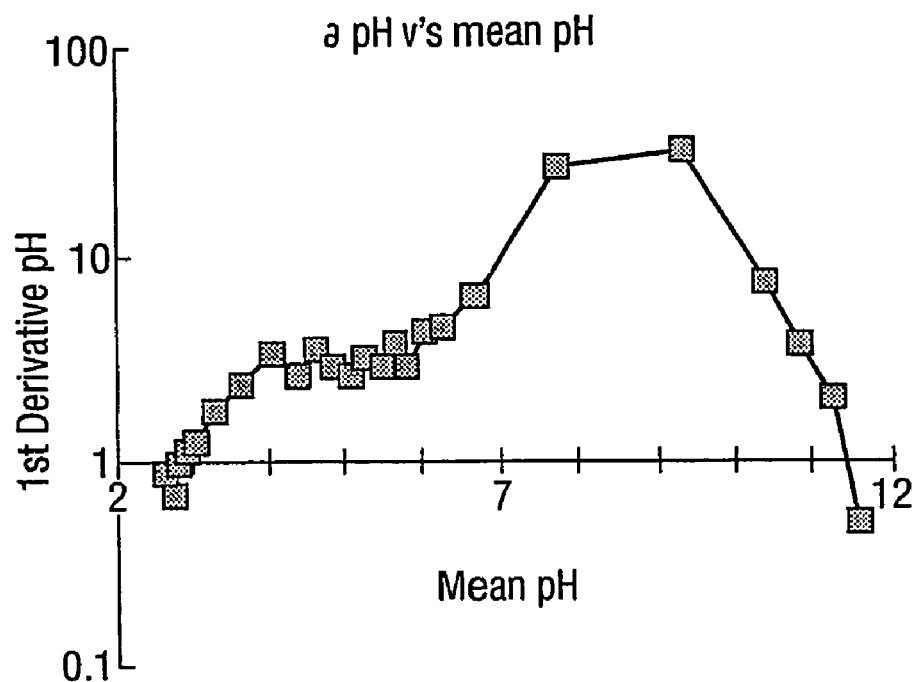
FIG. 1 shows the first derivative of pH versus pH in a solution of AQ4N dihydrochloride.
Figure 2:
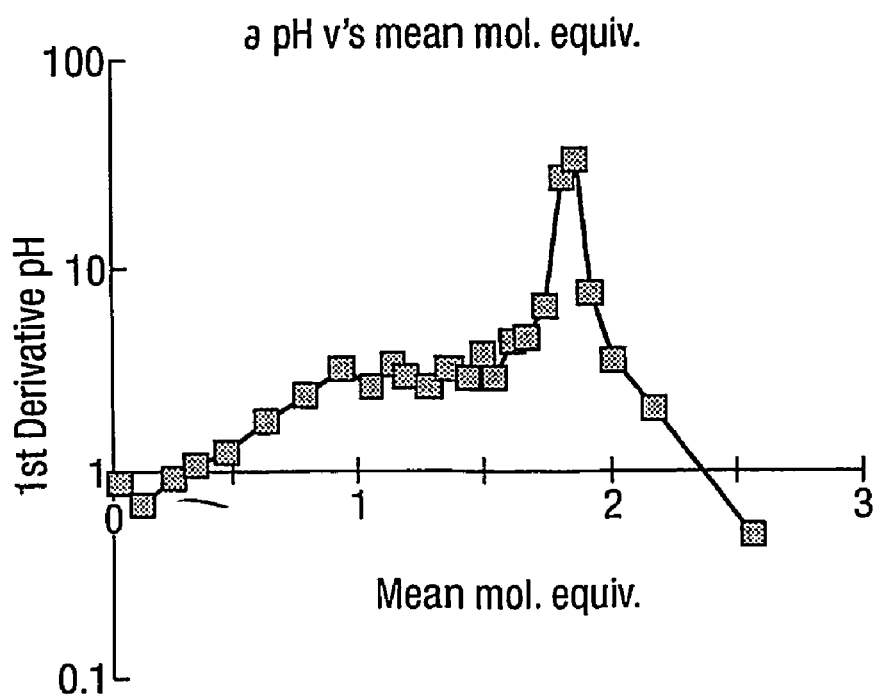
FIG. 2 shows the first derivative of pH versus NaOH molar equivalence under the same conditions.

Demonstration of the Instability of AQ4N Dihydrochloride—Physico-Chemical Properties of AQ4N Changes in the pH of a solution of AQ4N dihydrochloride were monitored to demonstrate the degradation of AQ4N into AQMN. The pH curves are shown in FIGS. 1 and 2. FIG. 1 shows a clear dissociation at between pH 7.7 and pH 9.4, and this equates to the dissociation events shown in FIG. 2 at approximately 2 molar equivalence. A low pH dissociation event can be observed, speculatively assigned to a pH between 4.1 and 4.6 where the molar equivalence is between 0.95 and 1.15.

Example 2

Demonstration of the Cytotoxicity of AQMN

The toxicity of a pure sample (99.3%) in the P388 system of AQ4N and AQMN were determined and the results obtained are presented in Table 2.

TABLE 2

AQ4N and AQMN cytotoxicity values

| Compound | IC$_{50}$ P388 (nM) | Relative toxicity (normalised to AQ4N) |
|---|---|---|
| AQ4N | 410 | 1.0 |
| AQMN | 77 | 5.2 |

Based on these data, AQMN has a cytotoxicity which is at least 5 times greater than that of AQ4N in the same system. The "greater than" modifier is required since all samples of AQ4N contain substantial percentages of AQMN, which will affect the toxicity result.

Example 3

Figure 3:
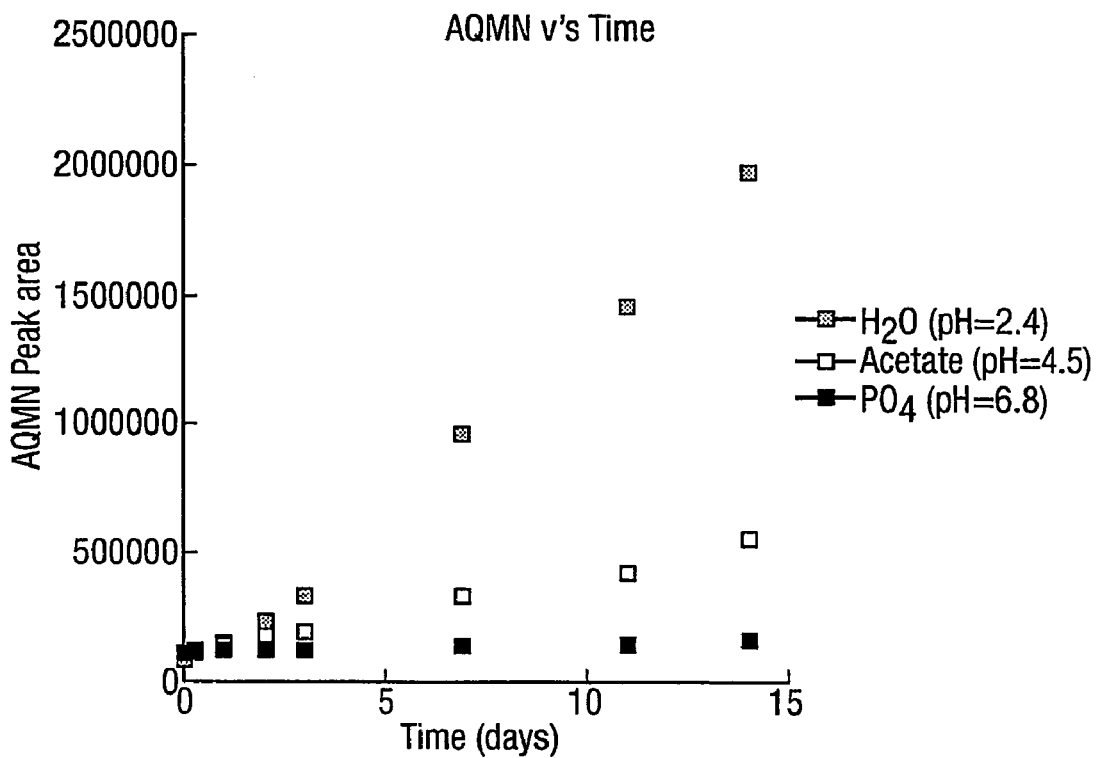
FIG. 3 shows the increase in AQMN over incubation time in 5 mg/ml solutions incubated at 40° C. for 14 days.

Demonstration of the Instability of AQ4N Dihydrochloride in Solution—Accumulation of AQMN The degradation of AQ4N was investigated using 5 mg/ml solutions of AQ4N at a pH of 2.4, 4.5 and 6.8, which equated to water, 20 mM sodium acetate buffer and 20 mM sodium orthophosphate buffer, respectively. The primary degradation pathway of AQ4N is its conversion to AQMN. The increase in AQMN concentration in 5 mg/ml solutions incubated at 40° C. over an intermediate time period (14 days) is shown in FIG. 3.

The degradation rates equate to a 0.84% (w.r.t. AQ4N), 0.19% (w.r.t. AQ4N) and 0.02% (w.r.t. AQ4N) increase in AQMN content per day under these conditions.

Using linear regression and cross correlating with the known quantity of AQMN in the material used as a standard these data indicate the accumulation rates of AQMN presented in Table 3.

TABLE 3

Accumulation of AQMN

| | H$_2$O | Acetate | PO$_4$ |
|---|---|---|---|
| AQMN increase per day | 0.84% | 0.19% | 0.02% |

Figure 4:
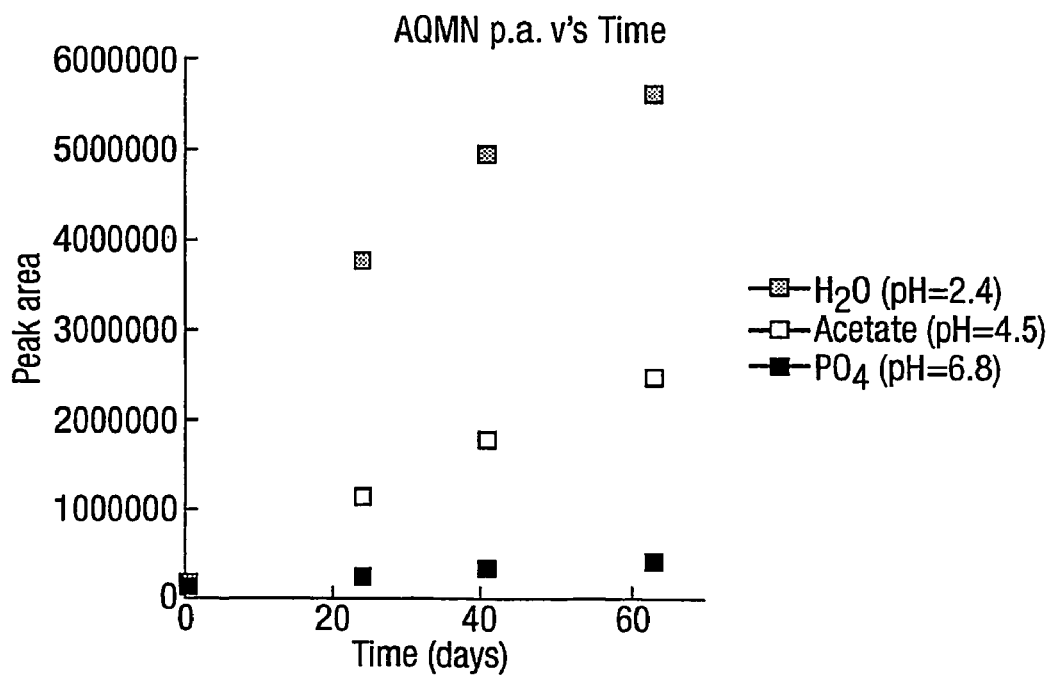
FIG. 4 shows the increase in AQMN over incubation time in 5 mg/ml solutions incubated at 40° C. for 63 days.

A similar trend was observed in the data after 63 days, as shown in FIG. 4. The rate of accumulation (calculated in the same way as above) shows that in the phosphate buffer AQMN increases by 0.6% per month.

Example 4

Demonstration of the Instability of AQ4N Dihydrochloride in Solution—Degradation of AQ4N The effect of pH on the stability of AQ4N was determined by investigating AQ4N degradation in different solutions. The solutions chosen were again distilled water, 20 mM sodium acetate buffer (pH=4) and 20 mM sodium phosphate buffer (pH=7). After preparation of the 5 mg/ml AQ4N buffered solutions the pH was corrected to the required pH of the buffer. The final pHs were 2.4, 4,5 and 6.8 for the distilled water, 20 mM sodium acetate buffer and 20 mM sodium phosphate buffer, respectively. The samples were incubated at 40° C. and sampled at regular intervals. Assay was carried out by sample dilution followed by HPLC analysis.

Figure 5:
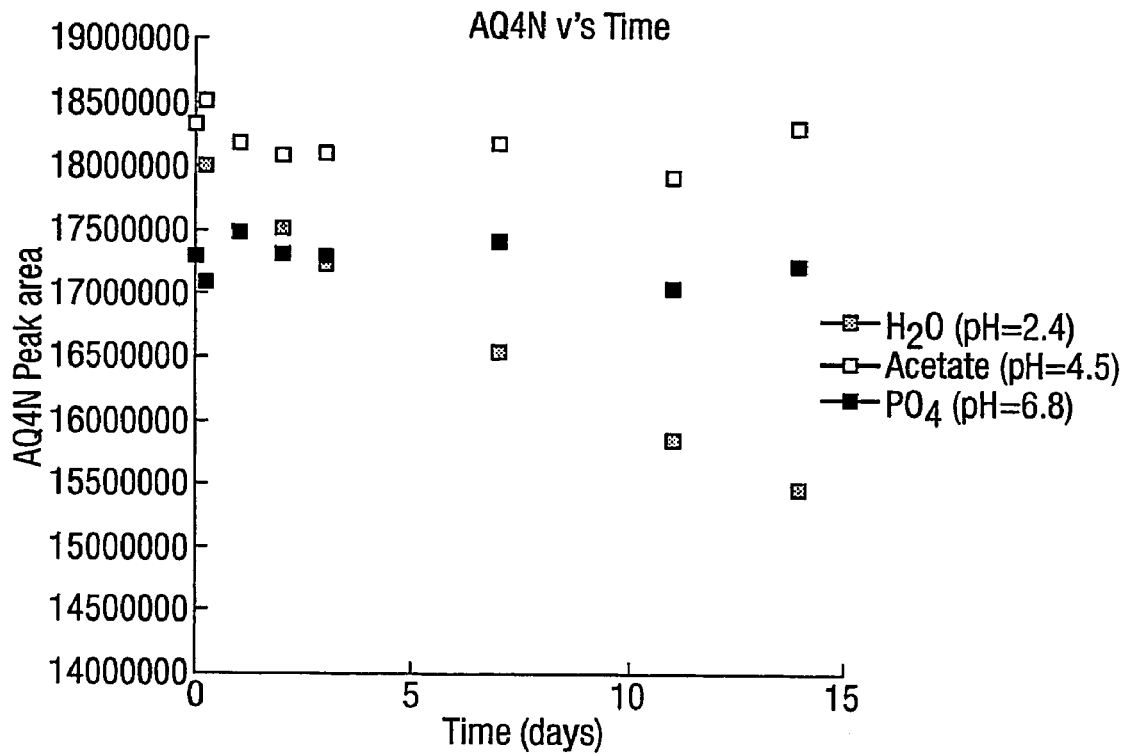
FIG. 5 shows the decrease in AQ4N over incubation time in 5 mg/ml solutions incubated at 40° C. for 14 days.

After 14 days an interim analysis was carried out with the data being shown in FIG. 5.

The solutions were further incubated at 40° C. for a total of 63 days. The final graph is shown in FIG. 6. The values obtained for the AQ4N contents are consistent with the quantities of AQ4N weighed into the origin a samples (within experimental error).

Example 5

Synthesis of Some Organic Acid Salts of AQ4N

A series of organic acid addition salts of AQ4N were prepared as shown formally in FIG. 7 and their stability with respect to AQMN formation was determined.

The choice of method for the synthesis of AQ4N salts was limited by the high solubility of AQ4N free base in polar solvents. Synthesis of malonic, citric, tartaric acid addition salts of AQ4N was initially attempted by adding an aqueous solution (1M) of the selected organic acid to a solution of AQ4N free base in a polar solvent/aqueous mixture such as H$_2$O/CH$_3$CN (1:1) or H$_2$O with a minimal amount of DMSO. After stirring for 2 hours, the reaction mixtures were cooled to 4° C. to facilitate precipitation. However, no solid was observed after 7 days. Subsequent work used MeOH as a solvent that readily to dissolve both AQ4N and all organic acids. In all cases except in the preparation of benzenesulfonic acid, the AQ4N was added to 20-fold excess of organic acid and these mixtures were left for 14-24 hours at room temperature and then at −10° C. to aid precipitation. If very little or no solid material was observed, diethyl ether was added to the mixture to facilitate precipitation.

Example 6

AQ4N Di-Benzenesulfonate

AQ4N (36 mg, 0.081 mmol) was dissolved in MeOH (5 mL) and stirred for 5 minutes. Benzenesulfonic acid (25.66 mg, 0.162 mmol) dissolved in 1 mL MeOH was added to the stirred solution of AQ4N. The reaction mixture was stirred for half an hour, and the precipitated solid was isolated by filtration. The dark blue solid was dried over phosphorous pentoxide under vacuum in a desiccator for 16 hours. Yield: 45 mg, 76%. Anal. calcd. for C$_{34}$H$_{40}$N$_4$O$_{12}$S: C, 56.04; H, 5.53; N, 7.69. Found: C, 55.80; H, 5.35; N, 9.30.

Example 7

AQ4N Di-Dichloroacetate

AQ4N (10 mg, 0.023 mmol) was dissolved in MeOH (1 mL) and stirred for 5 minutes. Dichloroacetic acid (38 μl, 0.46 mmol) was added to the stirred solution of AQ4N. The reaction mixture was stirred for 1 hour at room temperature followed by 16 hours at −10° C. The precipitated solid was isolated by filtration. The dark blue solid was dried over phosphorous pentoxide under vacuum in a desiccator for 16 hours. Yield: 7.4 mg, 46%. Anal. calcd. for C$_{26}$H$_{32}$N$_4$O$_{10}$Cl$_4$: C, 44.46; H, 4.59; N, 7.98. Found: C, 44.58; H. 4.61; N, 7.91.

Example 8

AQ4N Di-Maleate

AQ4N (10 mg, 0.023 mmol) was dissolved in MeOH (1 mL) and stirred for 5 minutes. Maleic acid (53.4 mg, 0.46 mmol) in MEOH (1 mL) was added to the stirred solution of AQ4N. The reaction mixture was stirred for 1 hour at room temperature followed by 16 hours at −10° C. The precipitated solid was isolated by filtration. The dark blue solid was dried over phosphorous pentoxide under vacuum in a desiccator for 16 hours. Yield: 7 mg, 47%. Anal. calcd. for $C_{30}H_{36}N_4O_{14}$: C, 53.24; H, 5.32; N, 8.28. Found: C, 53.11; H, 5.46; N, 8.20.

Example 9

AQ4N Di-Malonate

AQ4N (10 mg, 0.023 mmol) was dissolved in MeOH (1 mL) and stirred for 5 minutes. Malonic acid (47.9 mg, 0.46 mmol) in MEOH (1 mL) was added to the stirred solution of AQ4N. The reaction mixture was stirred for 1 hour at room temperature followed by 24 hours at −10° C. The precipitated solid was isolated by filtration. The dark blue solid was dried over phosphorous pentoxide under vacuum in a desiccator for 16 hours. Yield: 8.2 mg, 55%. Anal. calcd. for $C_{28}H_{36}N_4O_{14}$: C, 51.53; H, 5.56; N, 8.59. Found: C, 51.67; H, 5.56; N, 8.74.

Example 10

AQ4N Di-Tartrate

AQ4N (10 mg, 0.023 mmol) was dissolved in MeOH (1 mL) and stirred for 5 minutes. Tartaric acid (69.1 mg, 0.46 mmol) in MEOH (1 mL) was added to the stirred solution of AQ4N. The reaction mixture was stirred for 1 hour at room temperature followed by 16 hours at −10° C. The precipitated solid was isolated by filtration. The dark blue solid was dried over phosphorous pentoxide under vacuum in a desiccator for 24 hours. Yield: 8.5 mg, 50%. Anal. calcd. for $C_{30}H_{40}N_4O_{18}$: C, 48.39; H, 5.41; N, 7.52. Found: C, 48.34; H, 5.41; N, 7.67.

Example 11

AQ4N Di-Citrate

AQ4N (10 mg, 0.023 mmol) was dissolved in MeOH (1 mL) and stirred for 5 minutes. Citric acid (88.4 mg, 0.46 mmol) in MEOH (1 mL) was added to the stirred solution of AQ4N. The reaction mixture was stirred for 1 hour at room temperature followed by 16 hours at −10° C. Ether (2 mL) was added to the reaction mixture and set aside at −10° C. for another 3 hours. The precipitated solid was isolated by filtration. The dark blue solid was dried over phosphorous pentoxide under vacuum in a desiccator for 24 hours. Yield: 7.1 mg, 37%. Anal. calcd. for $C_{34}H_{44}N_4O_{20}$: C, 49.28; H, 5.10; N, 6.65. Found: C, 49.59; H, 5.09; N, 6.64.

Example 12

AQ4N Di-Lactate

AQ4N (10 mg, 0.023 mmol) was dissolved in MeOH (1 mL) and stirred for 5 minutes. Lactic acid (35 μl, 0.46 mmol) was added to the stirred solution of AQ4N. The reaction mixture was stirred for 1 hour at room temperature followed by 16 hours at −10° C. Ether (2 mL) was added to the reaction mixture and set aside at −10° C. for another 3 hours. The precipitated solid was isolated by filtration. The dark blue solid was dried over phosphorous pentoxide under vacuum in a desiccator for 24 hours. Yield: 4.5 mg, 31%. Anal. calcd. for $C_{28}H_{40}N_4O_{12}$: C, 53.84; H, 6.45; N, 8.97. Found: C, 51.54; H, 6.24; N, 8.89.

Example 13

AQ4N Di-Pimelate

AQ4N (10 mg, 0.023 mmol) was dissolved in MeOH (1 mL) and stirred for 5 minutes. Pimelic acid (73.7 mg, 0.46 mmol) in MeOH (1 mL) was added to the stirred solution of AQ4N. The reaction mixture was stirred for 1 hour at room temperature followed by 14 hours at −10° C. The precipitated solid was isolated by filtration. The dark blue solid was dried over phosphorous pentoxide under vacuum in a desiccator for 24 hours. Yield: 8.2 mg, 47%. Anal. calcd. for $C_{36}H_{52}N_4O_{14}$: C, 56.80; H, 6.80; N, 7.34. Found: C, 56.49; H, 6.41; N, 8.46.

Example 14

AQ4N Di-Acetate

AQ4N (70 mg, 0.158 mmol) was dissolved in MeOH (1 mL) and stirred for 5 minutes. Acetic acid (183 μl, 3.16 mmol) in MeOH (1 mL) was added to the stirred solution of AQ4N. The reaction mixture was stirred for 1 hour at room temperature followed by 18 hours at −10° C. Ether (3 mL) was added to the reaction mixture and set aside at −10° C. for another 3 hours. The precipitated solid was isolated by filtration. The dark blue solid was dried over phosphorous pentoxide under vacuum in a desiccator for 24 hours. Yield: 68 mg, 76%. %. Anal. calcd. for $C_{26}H_{36}N_4O_{10}$: C, 55.31; H, 6.43; N, 9.92. Found: C, 55.28; H, 6.57; N, 9.91.

Example 15

Determination of the pH of Organic Acid Salts of AQ4N in Aqueous Solution at 37° C.

Stock solutions of individual AQ4N salts were prepared by transferring about 1 mg, accurately weighed, and diluting with water to obtain solutions of 1.4 mM. The solution was vortexed for 3 min using a Fisons WhirlMixer™ (Loughborough, Leicestershire, UK). All AQ4N salt solutions were prepared on the same day as determination of the pH value of the solutions, which was done using a digital pH meter (calibrated at 21±1° C. with standard buffers of pH 7.00 and 4.00 from BDH (UK).

Table 4 and FIG. 7 shows the nine organic acids used to prepare salts of AQ4N in order of increasing $pK_{a1}$ values.

TABLE 4 pK$_{a1}$ of acids used to prepare salts of AQ4N and resulting pH of aqueous solutions

| Acid used to prepare AQ4N disalt | pK$_{a1}$ | pH[a] | Acid used to prepare AQ4N disalt | pK$_{a1}$ | pH[a] |
|---|---|---|---|---|---|
| Hydrochloric | ~−6 | 2.4 | Tartaric | 3.02 | 2.8 |
| Benzenesulfonic | −2.5 | 2.5 | Citric | 3.13 | 3.3 |
| Dichloroacetic | 1.25 | 2.4 | DL-Lactic | 3.86 | 3.5 |
| Maleic | 2 | 2.6 | Pimelic | 4.48 | 3.8 |
| Malonic | 2.85 | 2.8 | Acetic | 4.75 | 3.8 |

[a]measured pH of AQ4N di-salt solutions (1.4 mM).

pK$_a$ data are from "IUPAC Handbook of Pharmaceutical Salts, Properties, selection and Use", P. Heinrich Stahl, Camille G. Wermuth (Eds) VHCA Verlag Helvitica Chimica Acta, Zurich & Wiley-VCH, Weinheim Joint publ.) 2002.

For comparison the pK$_a$ for hydrochloric acid is also included. The organic acids used to prepare AQ4N salts in this study were:

Mono-acid: benzenesulfonic, dichloroacetic, lactic, acetic

Di-acid: maleic, malonic, tartaric, pimelic

Tri-acid: citric

The pK$_a$s of these acids are a measure of the degree of ionisation of each acid moiety and hence will reflect their acidity as measured by pH. Table 4 shows that the measured pH of the AQ4N salt (1.4 mM) solutions was as low as pH 2.4 & 2.5 for benzenesulfonate and dichloroacetate salts respectively and pH 3.8 for acetate and pimelate salts.

Example 16

Determination of the Purity of Organic Acid Salts of AQ4N in Aqueous Solution at 37° C.

The chromatographic separation of AQ4N salt solutions were performed using a gradient mobile phase and a HiChrom HIRPB (250 mm×4.6 mm, 5 μm) column (HiChrom, Agilent, Reading, UK, P/N HIRPB-6294) housed into a Flatron Column Heater system at 24° C. The mobile phase used for the gradient separation of AQ4N salts consisted of solvent system A (5% acetonitrile 95% ammonium formate buffer (0.05M, pH 3.6) and solvent system B (50% acetonitrile 50% ammonium formate (0.05M, pH 3.6). The pH was adjusted to 3.6 with formic acid. The gradient was run from 20% mobile phase A to 95% mobile phase B over 55 minutes. A flow rate of 1.3 ml min$^{-1}$ was used for all separations. Data were collected using λ=612 nm and the data were processed using Waters Millennium$^{32TM}$software.

Freshly prepared solutions of the prepared AQ4N salts (1.4 mM) were chromatographed within 30 min of dissolution. All the AQ4N salts were shown to be predominantly AQ4N (greater than 99%) with less than 1% the mono-N-oxide AQ4M or AQMN.

The invention claimed is:

1. A compound of formula (I):

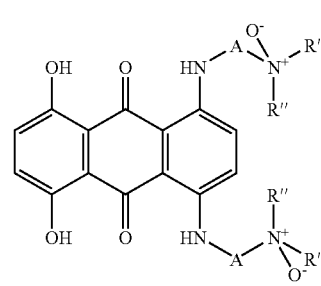

in which A is a C alkylene group with a chain length between NH and N(O)R'R" of at least 2 carbon atoms and R' and R" are each separately selected from C$_{1-4}$ alkyl groups and C$_{2-4}$ hydroxyalkyl and C$_{2-4}$ dihydroxyalkyl groups in which the carbon atom attached to the nitrogen atom does not carry a hydroxy group and no carbon atom is substituted by two hydroxy groups, or R' and R" together are a C$_{2-6}$ alkylene group which with the nitrogen atom to which R' and R" are attached forms a heterocyclic group having 3 to 7 atoms in the ring, wherein the compound is in the form of a salt with a physiologically acceptable acid having a pK$_a$ in the range of 2.0 to 9.0.

2. A compound as claimed in claim 1 wherein the physiologically acceptable acid has a pK$_a$ in the range of 2.0 to 6.0.

3. A compound as claimed in claim 2 wherein the physiologically acceptable acid has a pK$_a$ in the range of 3.0 to 6.0.

4. A compound as claimed in claim 1 wherein the physiologically acceptable acid is an organic mono-, di- or tri-acid.

5. A compound as claimed in claim 1 wherein the physiologically acceptable acid is selected from the group consisting of tartaric acid, malonic acid, dichloroacetate acid, citric acid, maleic acid, benzenesulfonic acid, pimelic acid and acetic acid.

6. A compound as claimed in claim 1 wherein A is a straight chain alkylene group.

7. A compound as claimed in claim 1 wherein A is ethylene.

8. A compound as claimed in claim 1 wherein R' and R" are straight chain alkyl groups or hydroxy-substituted alkyl groups.

9. A compound as claimed in claim 8 wherein R' and R" are each CH$_3$ or CH$_2$CH$_3$.

10. A compound as claimed in claim 9 wherein each group of formula NH-A-N(O)R'R" is group of formula NH—(CH$_2$)$_2$—N(O)(CH$_3$)$_2$.

11. A compound as claimed in claim 1 wherein the compound is formulated in a mixture containing additional components so that upon dissolution in aqueous solution the pH of the solution is buffered to be in the range of 5 to 9.

12. An aqueous solution of a compound as claimed in claim 1 wherein the pH of the solution is in the range of 5 to 9.

13. A pharmaceutical composition comprising a compound of formula (1) as defined in claim 1 together with a physiologically acceptable diluent or carrier.

14. Method of treating cancer in a warm blooded animal comprising administering to said animal an effective amount of a compound of formula (I) as claimed in claim 1, wherein said cancer is selected from the group consisting of breast cancer, lung cancer, prostate cancer, pancreatic cancer, esophageal cancer, non-Hodgkin's lymphoma and acute non-lymphocytic leukemia.

* * * * *